US009750637B2

(12) United States Patent
Schaller

(10) Patent No.: US 9,750,637 B2
(45) Date of Patent: Sep. 5, 2017

(54) ASPIRATION DEVICE WITH VACUUM LIMITER

(71) Applicant: NOVARTIS AG, Basel (CH)

(72) Inventor: Philipp Schaller, Stein am Rhein (CH)

(73) Assignee: NOVARTIS AG (CH)

( * ) Notice: Subject to any disclaimer, the term of this patent is extended or adjusted under 35 U.S.C. 154(b) by 364 days.

(21) Appl. No.: 14/696,913

(22) Filed: Apr. 27, 2015

(65) Prior Publication Data

US 2016/0310322 A1 Oct. 27, 2016

(51) Int. Cl.
*A61F 9/007* (2006.01)
*A61M 1/00* (2006.01)

(52) U.S. Cl.
CPC ....... *A61F 9/00736* (2013.01); *A61M 1/0045* (2014.02); *A61M 1/0047* (2013.01); *A61M 2210/0612* (2013.01)

(58) Field of Classification Search
CPC .............. A61M 1/0045; A61M 1/0047; A61M 2210/0612
See application file for complete search history.

(56) References Cited

U.S. PATENT DOCUMENTS 5,335,655 A * 8/1994 Kee ..................... A61M 1/0031
116/138
5,730,727 A * 3/1998 Russo ................. A61M 1/0047
137/517

OTHER PUBLICATIONS

Alcon brochure, "Grieshaber Advanced Backflush DSP Coming Soon," Sep. 21, 2010, 2 pages.

* cited by examiner

*Primary Examiner* — Tatyana Zalukaeva
*Assistant Examiner* — Kai Weng

(57) ABSTRACT

Systems, devices, and methods include a hand-held instrument with an aspiration conduit extending therethrough and with an aspiration needle arranged to aspirate fluid from a surgical site. A vacuum limiter is associated with the aspiration conduit. The vacuum limiter includes an opening formed in a wall of the aspiration conduit, an actuator disposed in the opening, and a biasing element biasing the actuator to a closed position that prevents passage of fluid through the opening. The biasing element is arranged to permit the actuator to displace from the closed position to a relief position so that fluid passes through the opening when a threshold vacuum is reached within the lumen. The actuator can further displace to an override position that prevents passage of fluid through the opening.

20 Claims, 4 Drawing Sheets

US 9,750,637 B2

ASPIRATION DEVICE WITH VACUUM LIMITER

TECHNICAL FIELD

The present disclosure is directed to ophthalmic surgical devices, systems, and methods. More particularly, but not by way of limitation, the present disclosure is directed to devices, systems, and methods utilizing a microsurgical aspiration device with a vacuum limiter.

BACKGROUND

Vitreoretinal surgeries typically include continuous irrigation to, and continuous aspiration from, a surgical site undergoing treatment. Aspiration typically includes a vacuum used to remove fluid, tissue, and debris from the surgical site. However, care should be taken during aspiration to ensure that, along with the fluid, only debris and unattached tissue are drawn into the aspiration path. Without such care, tissue can become inadvertently incarcerated into the aspiration path. Incarceration of tissue into the aspiration path may cause additional surgical setbacks to be overcome during the surgery. For example, when fluid is removed from a subretinal space in retinal detachment treatments, the retina may become vacuumed in the port of the aspiration tip. This can, for example, lead to enlargement of the retinal tear or tissue damage. Retinal incarceration can also occur when users place an aspiration tip of the instrument underneath a detached retina to remove subretinal fluid. Since the visibility through the detached retina is limited, the user risks incarcerating tissue since he or she may not see the instrument tip clearly. It can also occur when the operator aspirates subretinal fluid close to a retinal break. Due to the fluid turbulences, the detached retina moves and can become incarcerated as well.

Some conventional treatment instruments permit a user to disrupt aspiration depending on hand or finger placement over a hole in the aspiration line. However, if the user does not react quickly enough in case of incarceration, tissue damage can occur. Further, if the user makes an unintended motion when tissue is incarcerated, it too can lead to retinal holes or to an enlargement of the retinal tear.

SUMMARY

In some exemplary aspects, the present disclosure is directed to an ophthalmic surgical system. The system may include a handle having a proximal end, a distal end, and an aspiration conduit defining an aspiration passageway. The system may also include an aspiration needle extending from the distal end of the handle. The aspiration needle may include a lumen in fluid communication with the aspiration passageway and an opening formed at a distal end of the needle. The opening may be arranged to aspirate fluid from a surgical site. A vacuum limiter may be associated with the aspiration conduit, and may include an opening, an actuator, and a biasing element. The opening may be formed in a wall of the aspiration conduit and may be in fluid communication with the aspiration passageway. The actuator may be disposed in the opening, and the biasing element may be arranged to bias the actuator to a closed position that prevents passage of fluid through the opening. The biasing element also may be structurally arranged to permit the actuator to displace from a closed position to a relief position so that fluid passes through the opening when a vacuum threshold is reached within the aspiration passageway.

In some aspects, the actuator may be moveable to an override position that substantially prevents passage of fluid through the opening. In some aspects, the actuator may be hour-glass shaped, and may include a narrow waist, a first end having a width greater than a width of the opening, and a second end having a width greater than a width of the opening. In some aspects, the first end may be disposed within the aspiration passageway and the second end may be disposed outside the aspiration passageway. In some aspects, the first end may include a sealing surface engageable with an inner surface of the aspiration conduit and the second end may include a sealing surface engageable with an outer surface of the aspiration conduit. In some aspects, the actuator may be formed of silicone. In some aspects, the biasing element may include a plurality of support legs that couple the actuator and the aspiration conduit. In some aspects, the biasing element may include a spring element. In some aspects, the aspiration conduit may include a peak, and the opening may be formed in the aspiration conduit at the peak. In some aspects, the handle may include a handle opening, and the actuator may be accessible at the handle opening. In some aspects, the system may also include an aspiration line extending from the handle and in fluid communication with the aspiration passageway. The system also may include a vacuum source in fluid communication with the aspiration line and configured to generate a vacuum in the aspiration line, the aspiration passageway, and the lumen of the aspiration needle.

In other exemplary aspects, the present disclosure is directed to another ophthalmic surgical system. This system may include a handle sized and shaped for grasping by a user, and including a proximal end, a distal end, and an aspiration conduit defining an aspiration passageway. The aspiration conduit may extend from the proximal end to the distal end. An aspiration needle may extend from the distal end of the handle. The aspiration needle may include a lumen and an opening in fluid communication with the lumen. The opening may be arranged to aspirate fluid from a surgical site. The lumen may be in fluid communication with the aspiration passageway. A vacuum limiter may be associated with the aspiration conduit and may include an opening and an actuator. The opening may be formed in a wall of the aspiration conduit so that the aspiration passageway is in communication with an exterior of the aspiration conduit. The actuator may be disposed in the opening and may be moveable between a closed position that prevents passage of fluid through the opening in lower vacuum scenarios, a relief position that permits the flow of fluid through the opening in higher vacuum scenarios, and an override position that prevents passage of fluid through the opening during the higher vacuum scenarios.

In some aspects, the system may include a biasing element that biases the actuator in the closed position. The biasing element may be structurally arranged to permit the actuator to displace to the relief position when a threshold vacuum is reached within the aspiration passageway. In some aspects, the actuator is hour-glass shaped with a narrow waist, a first end having a width greater than a width of the opening, and a second end having a width greater than a width of the opening. In some aspects, the first end may be disposed within the aspiration passageway and the second end may be disposed outside the aspiration passageway. In some aspects, the first end includes a sealing surface engageable with an inner surface of the aspiration conduit. The second end may include a sealing surface engageable with an outer surface of the aspiration conduit. In some aspects, the biasing element may include a plurality of support legs that couples the aspiration conduit and the actuator.

In yet other exemplary aspects, the present disclosure is directed to methods of using an ophthalmic surgical system. Some exemplary methods may include grasping a handle of a surgical device. The handle may include a proximal end, a distal end, and an aspiration conduit defining an aspiration passageway. The method may also include introducing an aspiration needle of the surgical device to a surgical site. The aspiration needle may extend from the distal end of the handle, and may include a lumen and an opening providing fluid communication between the surgical site and the lumen. The lumen may be in fluid communication with the aspiration passageway. The method may also include aspirating fluid through the aspiration passageway at an initial vacuum level with a vacuum limiter in a closed position, with the vacuum limiter being arranged to automatically move from the closed position to a relief position that permits the flow of fluid through an opening in the aspiration conduit when the vacuum increases beyond a vacuum threshold that is greater than the initial vacuum level.

In some aspects, the method may also include selectively depressing the actuator of the vacuum limiter from the relief position that permits the flow of fluid through an opening in the aspiration conduit to an override position that prevents passage of fluid through the opening during said higher vacuum scenario. In some exemplary aspects, the vacuum limiter comprises an actuator having a wide first end, a second end, and a narrow waist between the first end and the second end, wherein the first end and the second end are larger than the opening in the aspiration conduit.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

Figure 1:
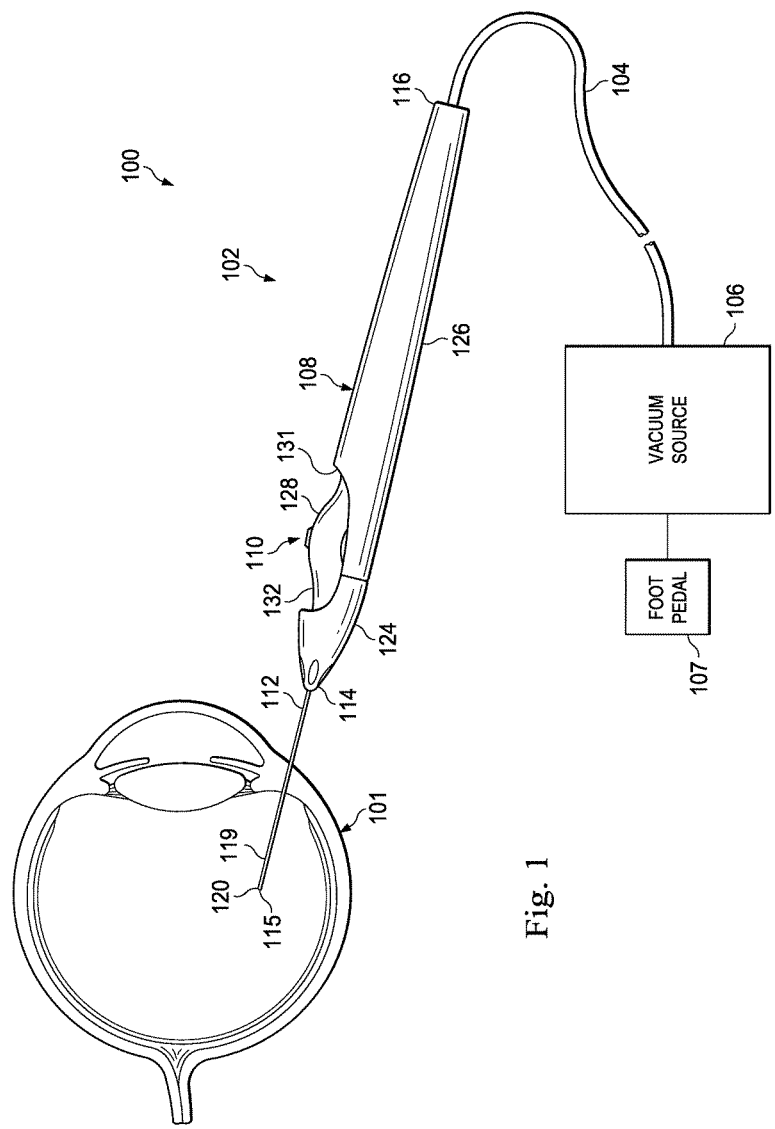
FIG. 1 is an illustration of an example ophthalmic surgical system, including an example microsurgical aspiration device.

These figures will be better understood by reference to the following detailed description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one or more implementations may be combined with the features, components, and/or steps described with respect to other implementations of the present disclosure. For simplicity, in some instances the same reference numbers are used throughout the drawings to refer to the same or like parts.

The present disclosure relates generally to devices, systems, and methods for using a mechanical vacuum limiter in an aspiration passage to reduce the vacuum in a microsurgical aspiration device. This is particularly useful when the microsurgical aspiration device has incarcerated or is otherwise acting on a detached retinal tissue. Relief of the vacuum may allow a user to more safely detach from the tissue without further exacerbating the tear by creating an additional tissue hole or enlarging the tear.

To achieve this, the mechanical vacuum limiter may comprise a valve that automatically opens to a relief position as soon as the vacuum inside the aspiration passage exceeds a defined limit. The open vacuum limiter reduces the vacuum in the aspiration passage by in-taking air from the environment. In addition, if the user wants to maintain a high vacuum, he or she can close the valve by mechanically depressing an actuator of the limiter, such as with a finger, to prevent vacuum relief.

The devices, systems, and methods of the present disclosure provide numerous advantages over conventional systems. For example, some implementations of the microsurgical aspiration device automatically turn off or reduce aspiration flow at the surgical site by opening the vacuum limiter when the vacuum exceeds a particular limit or threshold. In addition, some implementations of the microsurgical aspiration device are flexible in operation by allowing a user to keep the vacuum high if desired by putting his finger on the vacuum limiter.

FIG. 1 illustrates an example ophthalmic surgical system 100 performing a treatment at a surgical site, shown as an eye 101. The system 100 may be used in various ophthalmic procedures, such as an anterior segment procedure, a posterior segment procedure, a vitreoretinal procedure, a vitrectomy procedure, a cataract procedure, and/or other desired procedures. Further, while the procedures identified are all ophthalmic procedures, other implementations are suited to work on other instruments that may be used to treat other aspects or regions of the body. For example, the systems, methods, and apparatuses described herein may be used in any procedure requiring aspiration at a surgical site.

The system 100 may include a handheld microsurgical aspiration device 102, an aspiration line 104, and a vacuum source 106. The aspiration device 102 may include a gripping portion or handle 108, a mechanical vacuum limiter 110, and an aspiration needle 112.

The handle 108 may be sized and shaped for grasping by a user and may be easily held and manipulated during a surgical process. It may be made of any desired or suitable material, and may be formed by any method, such as, for example, injection molding or machining. In some examples, the handle 108 may be made of a thermoplastic or a metal material. Also, a portion of the handle 108 may be textured or knurled to improve gripping. The handle 108 includes a distal end 114 and a proximal end 116 and, in the example shown, includes the vacuum limiter 110 disposed on the handle 108 closer to the distal end 114 than the proximal end 116.

In the exemplary implementation shown in FIG. 1, the handle 108 is formed of multiple pieces joined together and includes a distal piece 124 connected to a proximal piece 126. Depending on the implementation, either or both of the distal and proximal pieces 124, 126 may be formed of a plurality of pieces. However, the scope of the disclosure is not so limited. Rather, in other implementations, the handle 108 may be formed from a single, unitary component.

The mechanical vacuum limiter 110 may be a valve actuatable to control or regulate the amount of vacuum applied at the needle 112. It may be actuatable to relieve the vacuum by permitting air from the outside environment to enter an aspiration passage in the handle 108. The vacuum limiter 110 is described in greater detail with reference to FIGS. 2-4 further below.

Depending on the implementation, the aspiration needle 112 may be a rigid cannula having a lumen and is configured to be inserted into or through tissue or through a cannula, such as a sclerotomy cannula, to a desired aspiration treatment location. The aspiration needle 112 may include an opening 115 that is in fluid communication with the lumen and may be configured to aspirate fluid from the aspiration location into the handle 108 for conveyance to the vacuum source 106. Some implementations of the aspiration needle 112 include a distal needle tip 120 formed as a soft tip that is configured to flex to protect damage to sensitive areas, such as the retina. Other implementations include a more rigid or a blunt end configured to provide stability or rigidity to the user. Yet other implementations include other types of distal tips. Further, the opening 115 may be formed in the distal needle tip 120 of the needle 112. In other instances, the opening 115 may be formed along an exterior surface 119 of the needle. Still further, the needle 112 may include multiple openings 115 formed therein. For example, the needle 112 may include an opening 115 disposed at the distal needle tip 120 along with one or more openings 115 formed in the exterior surface 119. In other instances, the needle 112 may include multiple openings 115 formed in the exterior surface 119 but not include an opening in the distal needle tip 120.

The aspiration line 104 may be a flexible vacuum hose that extends from the proximal end 116 of the handle 108 to the vacuum source 106. The vacuum source 106 is configured to create a vacuum in the aspiration line 104, which creates a vacuum in the handle 108 and in the aspiration needle 112 for treatment of a surgical site. In some implementations, the vacuum source 106 is or forms a part of a surgical console (not shown) that includes additional functionality for the treatment of a patient. For example, the console may also provide for control of an irrigation portion, a vitrectomy portion, an illumination light, an ultrasonic treatment system, or other suitable elements that may be used in ophthalmic or other surgical procedures. Some implementations include a foot pedal 107 that may be pressed or actuated to control the vacuum source 106. For example, when the vacuum source 106 is a part of a surgical console, the foot pedal 107 may communicate with the console to regulate the vacuum level to control aspiration through the aspiration device 102.

Figure 2:
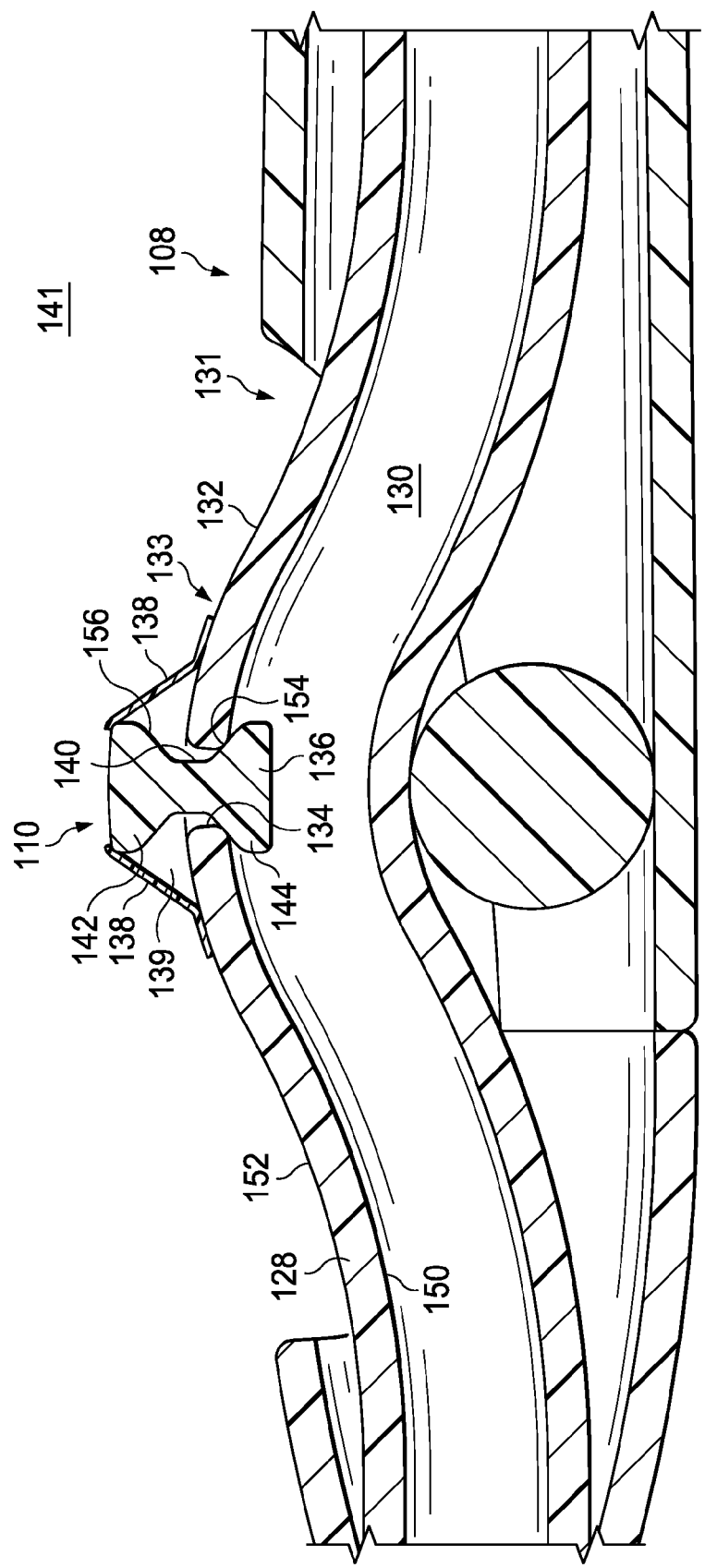
FIG. 2 is a cross-sectional illustration of a vacuum limiter of the example microsurgical aspiration device in a closed position to control the aspiration vacuum.
Figure 3:
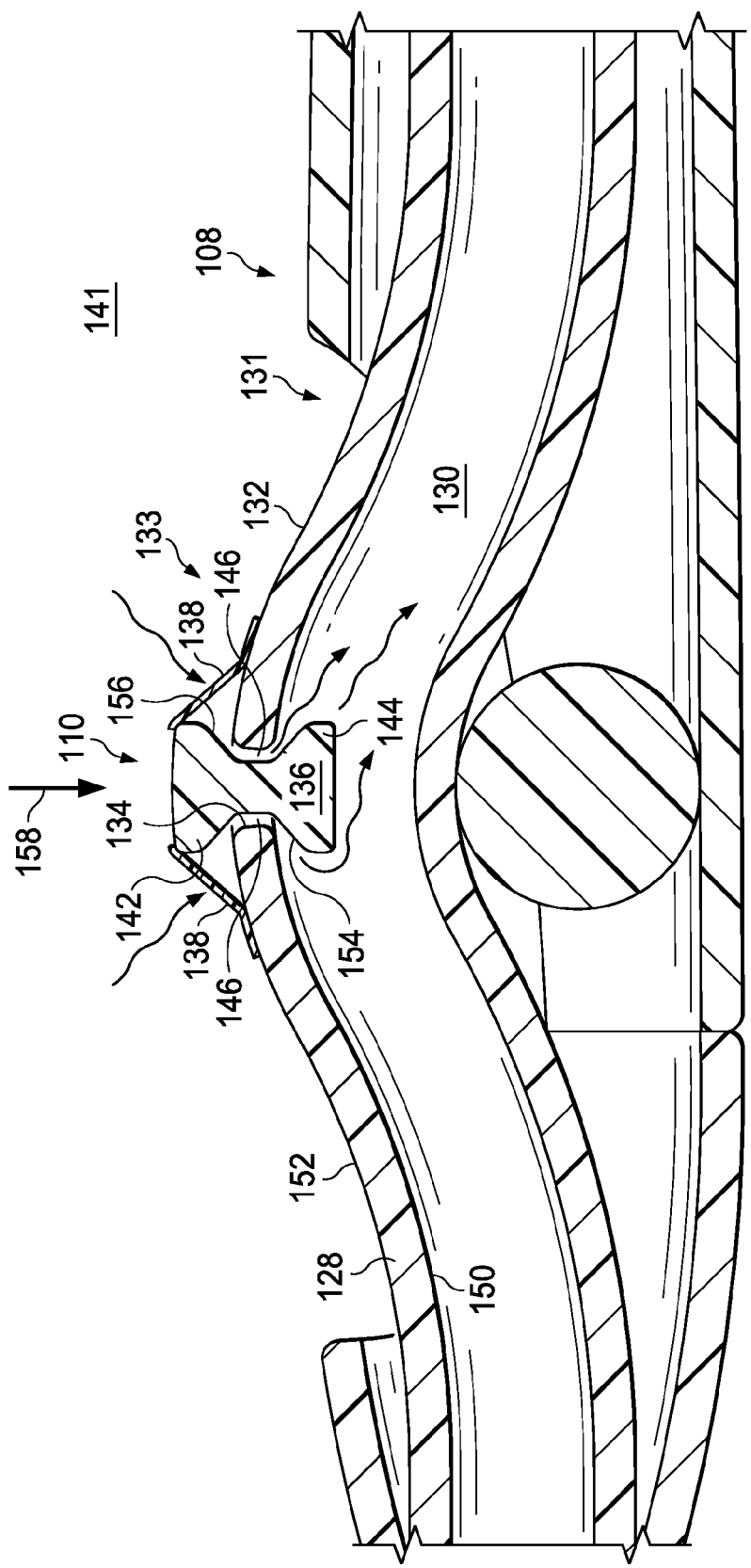
FIG. 3 is a cross-sectional illustration of the vacuum limiter of the example microsurgical aspiration device in a relief position to release the vacuum.
Figure 4:
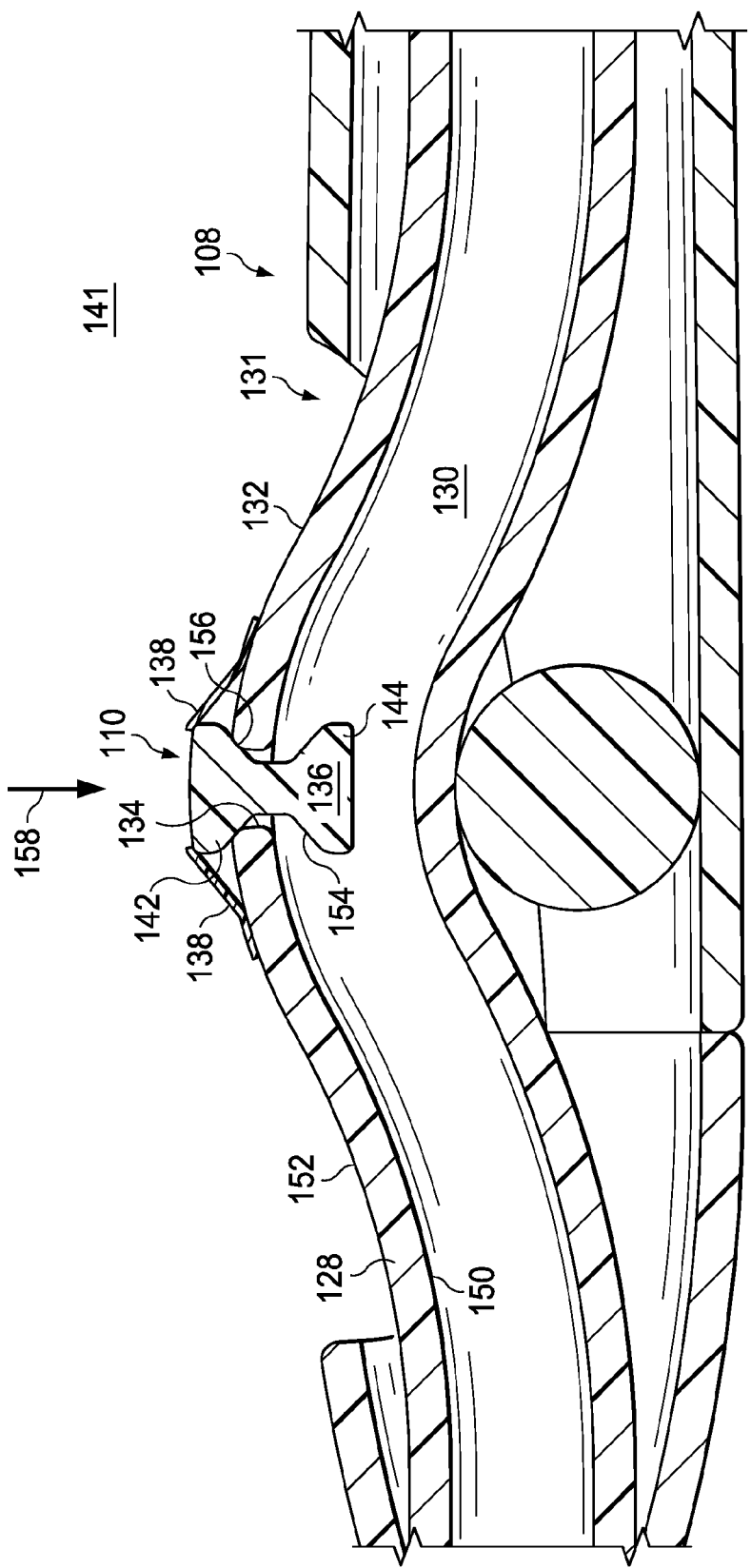
FIG. 4 is a cross-sectional illustration of the vacuum limiter of the example microsurgical aspiration device in an override position to retain the vacuum.

FIGS. 2-4 show cross-sectional views of the handle 108 and the vacuum limiter 110. As can be seen in FIG. 2, the handle 108 includes an aspiration conduit 128 having an aspiration passageway 130. The aspiration conduit 128 may be formed of vacuum tubing or a more rigid housing. The aspiration passageway 130 is in fluid communication with the aspiration line 104 and the lumen of the aspiration needle 112 shown in FIG. 1. In the exemplary implementation shown in FIG. 1, the handle 108 includes an opening 131 along a lateral side portion through which a projecting portion 132 of the aspiration conduit 128 may be accessed by a user. At the peak or apex 133 of the projecting portion 132, the aspiration conduit 128 includes an opening 134 to the outer environment, extending from an inner facing surface 150 to an outer facing surface 152 of the aspiration conduit 128. In this implementation, the opening 134 is a circular opening. However, in other implementations, the opening 134 may be oval shaped or have some other shape. While the illustrated example handle 108 is shown with the aspiration conduit 128 having a peak or apex 133, in other implementations, the aspiration conduit 128 may include a more cylindrical or even flat portion about the opening 134.

An actuator 136 is disposed within the opening 134 and moveable within the opening 134 to different positions. In this implementation, the actuator 136 is moveable in a direction transverse to the longitudinal or flow direction of the aspiration conduit 128. In the exemplary implementation shown in FIG. 2, the shape of the actuator 136 helps secure the actuator 136 in the opening 134. In this example, the actuator 136 has an hour-glass shape, with a narrow waist 140, a wide outer end 142, and a wide inner end 144. The inner end 144 is disposed within the aspiration passageway 130 of the aspiration conduit 128 and the outer end 142 is disposed outside the aspiration passageway 130 in the atmospheric environment. The inner end 144 includes a sealing surface 154 arranged to selectively engage the inner facing surface 150 of the aspiration conduit 128. The outer end 142 includes a sealing surface 156 arranged to selectively engage the outer facing surface 152 of the aspiration conduit 128. The waist 140 has a length greater than the thickness of a wall of the aspiration conduit 128. This allows the actuator 136 to be displaced, such as by axial translation, from a position where the sealing surface 154 of the inner end 144 is engaged with the aspiration conduit 128 and where the sealing surface 156 of the outer end 142 is not engaged with the aspiration conduit 128 to a position where the sealing surface 154 of the inner end 144 is not engaged with the aspiration conduit 128 and where the sealing surface 156 of the outer end 142 is engaged with the aspiration conduit 128. The actuator 136 may also be displaced such that neither the sealing surface 154 nor the sealing surface 156 is engaged with the aspiration conduit 128.

The actuator 136 may be formed of any suitable material, and in some implementations, is formed of a flexible or elastomeric material. In some implementations, the actuator 136 is formed of a silicone material. The material may be selected to seal against the aspiration conduit 128 so as to selectively prevent communication from the outside environment into the aspiration passageway 130 of the aspiration conduit 128 through the opening 134.

One or more biasing elements 138 may connect the projecting portion 132 to the actuator 136 and bias the actuator 136 in a particular position. In the illustrated implementation, the one or more biasing elements 138 bias the projecting portion 132 to an outer-most position away from the aspiration passageway 130, defining a closed position. The one or more biasing elements 138 may be formed of one or more support legs, such as one or more leaf spring elements, or one or more other biasing elements, such as, for example, one or more coil spring elements, compliant mechanisms, rubber dampeners, or other biasing elements that provide a biasing force. In some implementations, the one or more biasing elements 138 may be formed of a metal material. In other instances, the one or more biasing elements 138 may be formed of a polymeric material. Yet other materials are also contemplated. The one or more biasing elements 138 provide fluid communication between the atmosphere 141 and the actuator 136. Thus, gas, such as air, may freely pass between the atmosphere 141 and a space 139 adjacent the actuator 136. Accordingly, the one or more biasing elements 138 are structurally arranged and connected with the projecting portion 132 in a manner that permits the free flow of air or other atmospheric relief fluid to the actuator 136 and ultimately through the opening 134.

The actuator 136 is moveable within the opening 134 between a closed position (shown in FIG. 2), a relief position (shown in FIG. 3), and an override position (shown in FIG. 4). FIG. 2 shows the actuator 136 in the closed position. In this position, the sealing surface 154 of the inner end 144 sealingly engages the inner facing surface 150 of the aspiration conduit 128 in a manner that prevents fluid communication between the aspiration passageway 130 and the outside environment. The one or more biasing elements 138 bias the actuator 136 to the position shown in FIG. 2. Because of this, aspiration fluid flow through the needle 112 (FIG. 1), the aspiration conduit 128, and the aspiration line 104 (FIG. 1) is unimpeded and is controlled via the vacuum source. A user, such as a medical professional, may use an input device, such as the foot pedal 107 discussed above, to control the vacuum source and, hence, the vacuum applied to the aspiration device 102. Accordingly, with the actuator 136 in the closed position shown in FIG. 2, full vacuum pressure is maintained within the aspiration passageway 130.

FIG. 3 shows the actuator 136 in the relief position and displaced from the closed position shown in FIG. 2. In the relief position, the actuator 136 is positioned such that the opening 146 provides fluid communication between the exterior of the aspiration conduit 128 and the aspiration passageway 130. This fluid communication reduces the vacuum applied within the aspiration passageway 130 by permitting fluid, such as air, to pass into the aspiration passageway 130. In the illustrated implementation, the actuator 136 moves to the relief position by translating in the direction of arrow 158 further into the aspiration passageway 130. This movement of the actuator 136 separates the sealing surface 156 from sealing engagement with the aspiration conduit 128, thereby providing fluid communication between the exterior of the aspiration conduit 128 and the aspiration passageway 130. When fluid, such as air, flows through the opening 134, the aspiration flow at the distal needle tip 120 is effectively eliminated. This may allow a user to easily remove incarcerated tissue from the distal needle tip 120. In other implementations, displacement of the actuator 128 into the relief position may significantly reduce vacuum pressure applied to the aspiration needle 112 and, thus, significantly reduce aspiration flow therethrough. In still other implementations, an amount by which the vacuum within the aspiration device 102 may be proportional to an amount by which the actuator 136 is displaced within the opening 146 relative to the aspiration conduit 128.

In some implementations, the actuator 136 is automatically moved into the relief position when the vacuum within the aspiration passageway 130 exceeds a vacuum threshold. The vacuum threshold may, for example, be a pre-established vacuum level that borders a safe zone of vacuum pressure. When the vacuum within the aspiration passageway 130 reaches or exceeds the vacuum threshold, the actuator 136 may be displaced from sealing engagement with the aspiration conduit 128, permitting fluid communication between the atmosphere 141 and the aspiration passageway 130.

In some implementations, the vacuum threshold may be within a range of about, for example, 150 to 250 mmHg. In other implementations, the vacuum threshold may be larger or smaller pressure ranges that cover different pressures, e.g., higher or lower pressures. For example, the vacuum threshold may vary depending upon the viscosity of the medium to be aspirated. In still other implementations, the vacuum threshold may be single pressure rather than a pressure range.

By providing vacuum relief when the vacuum exceeds the vacuum threshold, the vacuum within the aspiration passageway 130 is prevented from exceeding a desired or acceptable level. This, in turn, may protect tissue that may be incarcerated, either intentionally or inadvertently, by the aspiration needle 112 during a procedure. For example, the vacuum within the aspiration passageway 130 may spike or otherwise increase when the opening 115 at the distal needle tip 120 may be occluded by tissue or other matter that restricts the fluid flow into the lumen of aspiration needle 112. If, during the vacuum spike, the vacuum exceeds the vacuum threshold, the actuator 136 is displaced to the relief position where atmospheric fluid is permitted to flow into the aspiration passageway 130 to maintain the vacuum at an acceptable level. Because the vacuum limiter 110 opens automatically in response to vacuum level, the vacuum limiter 110 reacts much more quickly in comparison to systems or mechanisms that require a manual response or reaction by a user.

The one or more biasing elements 138 may be designed or configured to facilitate displacement of the actuator 136 at a desired vacuum level within the aspiration passageway 130. For example, stiffer biasing elements 138 may result in a relatively higher vacuum threshold, while less rigid biasing elements 138 may result in a relatively lower vacuum threshold. Consequently, stiffer biasing elements 138 may correspond to displacement of the actuator 136 at a higher vacuum level, while less stiff biasing elements 138 may result in displacement of the actuator 136 at a relatively lower vacuum level.

In use, the vacuum within the aspiration conduit passageway 130 may spike or otherwise increase when the tip of the aspiration device 102 is occluded by tissue or other matter that restricts the flow of fluid into the needle 112. Other reasons may also exist that cause an increase in vacuum. However, regardless of what the cause of the fluctuation in vacuum within aspiration passageway 130 may be, the actuator 136 moves into the relief position when the vacuum level meets or exceeds the vacuum threshold.

FIG. 4 shows the actuator 136 in an override position. In the override position, a user manually disables vacuum relief to the aspiration passageway 130. A user may place the actuator 136 into the override position when the user desires to create a vacuum in the aspiration passageway 130 greater than the vacuum threshold. A user displaces the actuator 136 into the override position by manually exerting a load or force on the actuator 136, such as by pressing the actuator 136 with a finger. This load or force displaces the actuator 136 in the direction of arrow 158 further into the aspiration passageway 130 until the sealing surface 156 of the outer end 142 sealingly engages the outer facing surface 152 of the aspiration conduit 128. The seal created between the actuator 136 and the aspiration conduit 128 prevents the flow of fluid, such as atmospheric gases, from passing through the opening 134 and entering the aspiration passageway 130. Thus, the vacuum pressure within the aspiration passageway 130 remains unaffected. Accordingly, the vacuum within the aspiration passageway 130 may be controlled such that the vacuum pressure within the aspiration passageway 130 is permitted to rise above the vacuum threshold.

In some implementations, the user may quickly apply a large force on the actuator 136 to compress the vacuum limiter 110 to generate a reflux. During reflux, a portion of the vacuum limiter 110 or the projecting portion 132 of the aspiration conduit 128 is elastically deformed such that the volume of the aspiration conduit 128 is reduced and backflow through the aspiration device 102 occurs. As a result, a volume of the material occupying the aspiration device 102 is forced out of the opening 115 of the aspiration needle 112 and into the eye, releasing the occlusion at or near the distal needle tip 120 (FIG. 1).

Some implementations are arranged so that as soon as the load is removed from the actuator 136, the biasing elements 138 displace the actuator 136 from the override position back to the relief position or to the closed position depending on the vacuum level within the aspiration passageway 130. Other implementations are arranged so that when the actuator 136 is moved to the override position, the actuator remains in the override position so long as the vacuum is above a certain threshold.

In some implementations, the vacuum level that causes the actuator 136 to move from the closed position to the relief position is different than the vacuum level that causes the actuator to move from the relief position to the closed position. If the vacuum limiter 110 opened and closed at the same vacuum level, the vacuum limiter 110 might chatter as it opens and closes rapidly. To avoid this potentially undesirable result, the one or more biasing elements 138 may be arranged to permit the vacuum limiter 110 to open at a first vacuum level, but to close at a second vacuum level that is different from the first vacuum level.

In some implementations, the second vacuum level may be a lower absolute pressure than the absolute pressure defining the first vacuum level. For example only and without limitation, in some instances, the vacuum limiter 110 may be arranged to transition from the closed position to the relief position at a vacuum level of 250 mmHg. However, the vacuum limiter 110 may not return from the relief position to the closed position until the vacuum level decreases to 100 mmHg. Accordingly, in this example, the difference between these two levels is 150 mmHg. In some implementations, the difference between the first vacuum level and the second vacuum level may be in a range from about 75 mmHg to 200 mmHg. These values and ranges are provided as examples only, and other values and ranges are also contemplated. In some instances, the first and second vacuum levels and associated ranges may be determined by the physical construct of the biasing elements.

The present disclosure provides the improvement and benefit of an aspiration device that automatically and mechanically stops the aspiration flow at a distal needle tip by opening a vacuum limiter when a defined vacuum threshold is exceeded. In addition, the disclosure provides that a user can maintain an aspiration vacuum at a high level if desired by pressing with a finger on the vacuum limiter. In addition, a user is able to regulate the vacuum within an aspiration device by manipulating a foot pedal or surgical console, thereby avoiding the user from having to use a hand or finger thereof to control vacuum. This is particularly helpful when an aspiration device includes a curved aspiration needle which may be required to be turned about its axis to orient the tip in a desired location. Finger alignment is less of a concern when using the vacuum limiter described herein.

In operation, a user may perform a surgical technique using the surgical system 100 by preparing a surgical site for surgery, and then introducing the needle 112 to the surgical site. In the example of the eye 101, the needle 112 may be introduced to the globe of the eye either through a cannula or directly through tissue to treat a region of the eye, such as the retina. In order to maintain intraocular pressure, the surgical site may be irrigated at the same or a higher rate than the aspiration rate. Either one or both of aspiration and irrigation may be controlled by the foot pedal 107 shown in FIG. 1.

The vacuum limiter 110 may begin in the closed position, as shown in FIG. 2. In this position, a vacuum may be applied at the distal end 119 of the aspiration needle 112, and fluid, tissue, or debris may be aspirated from the surgical site through the opening 115 in the aspiration needle 112. If tissue occludes or becomes incarcerated in the opening 115 of the aspiration needle 112, fluid flow from the surgical site decreases, causing an increase in vacuum. When the vacuum increases beyond a preset vacuum threshold, the vacuum overcomes a biasing force of the one or more biasing elements 138 and displaces the actuator 136 from the closed position to the relief position. As a result, fluid, such as air from the atmosphere is permitted to enter the aspiration passageway 130, providing relieve to the vacuum. In response, the vacuum at the distal needle tip 120 decreases, and any tissue incarcerated in the opening 115 may be more easily removed therefrom or the distal needle tip 120 may simply be moved away from the tissue. As a result, risk of damage or harm to the incarcerated or surrounding tissues is reduced. Therefore, in the context of retinal surgical procedures, the risk of creating new or enlarging existing retinal holes or retinal tears is significantly reduced.

If a user desires to operate with a higher vacuum, the user can override the relief position by moving the actuator 136 into an override position. To do this, the user may apply a load or a force that overcomes the force of the one or more biasing elements 138 and moves the actuator 136 to the override position. This position prevents or substantially prevents fluid communication between the aspiration passageway 130 and the atmosphere 141. In this position, the user may be able to operate with a higher vacuum as desired. In some implementations, releasing the actuator 136 results in the actuator 136 returning to either the closed position or the relief position.

It should be understood that the biasing elements described herein, such as the biasing elements 138, may be used, by design, material, or structure, to achieve any desired biasing force, thereby enabling selection of a desired biasing force. Some surgical procedures may be more sensitive than others, and a user may select a microsurgical aspiration device of a type as described herein having one or more biasing elements with a biasing force commensurate with the type of procedure to be performed. For example, biasing elements that provide a low biasing force may be used in an aspiration device to be employed in a surgical procedure that is more sensitive to vacuum changes. Other surgical procedures may be less sensitive, and a user may select an aspiration device with biasing elements that provide a biasing force that is less sensitive to vacuum changes.

Accordingly, the systems, devices, and methods described herein may permit a user to perform a surgery in a manner more effective for vacuum control and more responsive to vacuum fluctuations.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical system, comprising:
   a handle comprising:
     a proximal end;
     a distal end; and
     an aspiration conduit defining an aspiration passageway;
   an aspiration needle extending from the distal end of the handle, the aspiration needle comprising:
     a lumen in fluid communication with the aspiration passageway; and
     an opening formed at a distal end of the needle, the opening arranged to aspirate fluid from a surgical site; and
   a vacuum limiter associated with the aspiration conduit, the vacuum limiter comprising:
     an opening formed in a wall of the aspiration conduit and in fluid communication with the aspiration passageway;
     an actuator disposed in the opening; and
     a biasing element biasing the actuator to a closed position that prevents passage of fluid through the opening, the biasing element being structurally arranged to permit the actuator to displace from a closed position to a relief position so that fluid passes through the opening when a vacuum threshold is reached within the aspiration passageway.

2. The system of claim 1, wherein the actuator is moveable to an override position that substantially prevents passage of fluid through the opening.

3. The system of claim 1, wherein the actuator is hour-glass shaped with:
   a narrow waist;
   a first end having a width greater than a width of the opening; and
   a second end having a width greater than a width of the opening.

4. The system of claim 3, wherein the first end is disposed within the aspiration passageway and wherein the second end is disposed outside the aspiration passageway.

5. The system of claim 4, wherein the first end includes a sealing surface engageable with an inner surface of the aspiration conduit, and wherein the second end includes a sealing surface engageable with an outer surface of the aspiration conduit.

6. The system of claim 1, wherein the actuator is formed of silicone.

7. The system of claim 1, wherein the biasing element comprises a plurality of support legs that couple the actuator and the aspiration conduit.

8. The system of claim 1, wherein the biasing element comprises a spring element.

9. The system of claim 1, wherein the aspiration conduit comprises a peak, and wherein the opening is formed in the aspiration conduit at the peak.

10. The system of claim 1, wherein the handle further comprises a handle opening, and wherein the actuator is accessible at the handle opening.

11. The system of claim 1, further comprising:
    an aspiration line extending from the handle and in fluid communication with the aspiration passageway; and
    a vacuum source in fluid communication with the aspiration line and configured to generate a vacuum in the aspiration line, the aspiration passageway, and the lumen of the aspiration needle.

12. An ophthalmic surgical system, comprising:
    a handle sized and shaped for grasping by a user, the handle comprising:
      a proximal end;
      a distal end; and
      an aspiration conduit defining an aspiration passageway, the aspiration conduit extending from the proximal end to the distal end;
    an aspiration needle extending from the distal end of the handle, the aspiration needle comprising:
      a lumen; and
      an opening in fluid communication with the lumen and arranged to aspirate fluid from a surgical site, the lumen being in fluid communication with the aspiration passageway;
    a vacuum limiter associated with the aspiration conduit, the vacuum limiter comprising:
      an opening formed in a wall of the aspiration conduit so that the aspiration passageway is in communication with an exterior of the aspiration conduit; and
      an actuator disposed in the opening and moveable between a closed position that prevents passage of fluid through the opening in lower vacuum scenarios, a relief position that permits the flow of fluid through the opening in higher vacuum scenarios, and an override position that prevents passage of fluid through the opening during the higher vacuum scenarios.

13. The ophthalmic surgical system of claim 12, further comprising a biasing element that biases the actuator in the closed position, the biasing element being structurally arranged to permit the actuator to displace to the relief position when a threshold vacuum is reached within the aspiration passageway.

14. The system of claim 12, wherein the actuator is hour-glass shaped with:
    a narrow waist;
    a first end having a width greater than a width of the opening; and
    a second end having a width greater than a width of the opening.

15. The system of claim 14, wherein the first end is disposed within the aspiration passageway and wherein the second end is disposed outside the aspiration passageway.

16. The system of claim 15, wherein the first end includes a sealing surface engageable with an inner surface of the aspiration conduit, and wherein the second end includes a sealing surface engageable with an outer surface of the aspiration conduit.

17. The system of claim 12, wherein the biasing element comprises a plurality of support legs that couples the aspiration conduit and the actuator.

18. A method of using an ophthalmic surgical system, comprising:
    grasping a handle of a surgical device, the handle comprising:
      a proximal end;

a distal end; and
an aspiration conduit defining an aspiration passageway;

introducing an aspiration needle of the surgical device to a surgical site, the aspiration needle extending from the distal end of the handle, the needle comprising a lumen and an opening providing fluid communication between the surgical site and the lumen, and the lumen being in fluid communication with the aspiration passageway; and aspirating fluid through the aspiration passageway at an initial vacuum level with a vacuum limiter in a closed position, the vacuum limiter being arranged to automatically move from the closed position to a relief position that permits the flow of fluid through an opening in the aspiration conduit when the vacuum increases beyond a vacuum threshold that is greater than the initial vacuum level.

19. The method of claim 18, further comprising selectively depressing the actuator of the vacuum limiter from the relief position that permits the flow of fluid through an opening in the aspiration conduit to an override position that prevents passage of fluid through the opening during said higher vacuum scenario.

20. The method of claim 18, wherein the vacuum limiter comprises an actuator having wide first end, a second end, and a narrow waist between the first end and the second end, wherein the first end and the second end are larger than the opening in the aspiration conduit.

* * * * *